United States Patent
Awad

(10) Patent No.: US 10,238,474 B2
(45) Date of Patent: Mar. 26, 2019

(54) DENTURE BITE RIM SYSTEM WITH REPLICA TEETH

(71) Applicant: Tony Joseph Awad, Orlando, FL (US)

(72) Inventor: Tony Joseph Awad, Orlando, FL (US)

( * ) Notice: Subject to any disclaimer, the term of this patent is extended or adjusted under 35 U.S.C. 154(b) by 0 days.

(21) Appl. No.: 15/217,394

(22) Filed: Jul. 22, 2016

(65) Prior Publication Data

US 2017/0304035 A1    Oct. 26, 2017

Related U.S. Application Data

(60) Provisional application No. 62/326,284, filed on Apr. 22, 2016.

(51) Int. Cl.
*A61C 13/34* (2006.01)
*A61C 13/01* (2006.01)
*A61C 13/107* (2006.01)

(52) U.S. Cl.
CPC .......... *A61C 13/34* (2013.01); *A61C 13/0001* (2013.01); *A61C 13/01* (2013.01)

(58) Field of Classification Search
CPC ................................ A61C 13/34; A61C 13/01
USPC .............................................. 433/26; 212/26
See application file for complete search history.

(56) References Cited

U.S. PATENT DOCUMENTS

| | | | | |
|---|---|---|---|---|
| 4,202,098 A * | 5/1980 | Russo | ................ | A61C 13/0025 433/168.1 |
| 5,639,235 A * | 6/1997 | Lapointe | .............. | A61C 13/082 433/215 |
| 6,422,864 B1 | 7/2002 | Glatt | | |
| 9,744,009 B2 * | 8/2017 | Liebman | ............... | A61C 9/0006 |
| 2002/0137000 A1 * | 9/2002 | Eggler | ................... | A61C 19/10 433/26 |
| 2010/0086899 A1 * | 4/2010 | Holzner | ............ | A61C 13/0004 433/199.1 |
| 2010/0283168 A1 * | 11/2010 | Vandor | .................. | A61C 13/12 264/17 |
| 2011/0129796 A1 * | 6/2011 | Riggio | ................ | A61C 9/0006 433/171 |
| 2013/0167380 A1 * | 7/2013 | Balshi | .................. | A61C 8/0048 29/896.1 |
| 2014/0000633 A1 * | 1/2014 | Hernandez | ............. | A61F 5/566 128/848 |
| 2014/0051037 A1 * | 2/2014 | Fisker | .................. | A61C 8/0048 433/213 |
| 2014/0080094 A1 * | 3/2014 | Howe | .................. | A61C 9/0053 433/191 |
| 2014/0170591 A1 * | 6/2014 | El-Siblani | ............. | A61C 13/34 433/36 |

(Continued)

*Primary Examiner* — Matthew M Nelson
(74) *Attorney, Agent, or Firm* — Jason T. Daniel, Esq.; Daniel Law Offices, P.A.

(57) ABSTRACT

A bite rim system includes a plurality of dental bite rims having a shape and size that is suitable for use in a human mouth. A plurality of anatomically correct replica teeth is constructed from wax, and also includes various tooth characteristics of different shapes, thicknesses, sizes and colors. A series of replica teeth are removably pre-mounted onto one or more of the bite rims in an anatomically correct pattern. The system also includes one or more replica teeth strips having a front facing surface with the image of one or more teeth imprinted thereon, and a back facing surface that is coated with an adhesive material for mating with one of the dental bite rims.

8 Claims, 4 Drawing Sheets

(56) References Cited

U.S. PATENT DOCUMENTS

2014/0272787 A1* 9/2014 Ginsburg ............ A61C 13/0004
433/171
2014/0356806 A1* 12/2014 Liebman ................ A61C 9/002
433/37

* cited by examiner

DENTURE BITE RIM SYSTEM WITH REPLICA TEETH

CROSS-REFERENCE TO RELATED APPLICATIONS

This application claims the benefit of U.S. Application Ser. No. 62/326,284 filed on Apr. 22, 2016, the contents of which are incorporated herein by reference.

TECHNICAL FIELD

The present invention relates generally to the field of dentistry, and more particularly a dental bite rim system with replica teeth.

BACKGROUND

The statements in this section merely provide background information related to the present disclosure and may not constitute prior art.

One of the most difficult aspects of constructing dental prosthesis containing artificial teeth such as dentures, for example, is ensuring a proper fit and a natural look. As it is common for patients and dentists to endure multiple visits before ending up with a satisfactory prosthesis. In this regard, during a first visit the dentist typically makes an impression of the patient's mouth which is sent to an offsite dental laboratory who then prepares a model of the impression. This model is returned to the dentist, along with a wax bite rim.

During a second appointment, the bite rims are aligned with the impression of the patient's mouth, and are adjusted by the dentist for proper fit. More specifically, the dentist looks to ensure the patient's jaws are comfortable, and that the patient can easily move their mouth while talking and chewing. During this time, the dentist will also make several anatomical marks on the bite rims that correspond to portions of the patient's mouth such as the patient's lip-line, smile-line and/or the mid-line, for example.

Next, the marked bite rims are sent back to the offsite dental laboratory where a dental technician sets a series of permanent dental artificial teeth into the marked bite rims, based on the anatomical marks provided by the dentist, and the same is then returned to the dentist for the patient to try and approve. This process is called the wax try-in stage, and is typically the most problematic portion of the entire process. This is because the dental technician preparing the dentures is never afforded the opportunity to see the patient. As such, the technician must make an educated guess about the characteristics of the permanent dental artificial teeth based solely from the markings on the bite rim. Several of these characteristics include, for example, an appropriate size and color of each artificial tooth, along with a particular shape such as oval, square, ovoid or round, for example.

For these and other reasons, it is common that during the following (third) appointment with the dentist, the patient dislikes some aspect of the prepared dental model, such as the shape, size and/or color of various teeth, for example. Such a situation commonly results in multiple follow up visits with the dentist and/or the dental laboratory to make adjustments to the permanent artificial teeth until the patient is satisfied. Such additional appointments and time (often weeks or months) results in dissatisfaction by the patient, and loss of revenue for the dentist and dental laboratory.

Accordingly, the present invention, directed to a dental bite rim system differs from the conventional art in a number of aspects. The manner by which will become more apparent in the description which follows, particularly when read in conjunction with the accompanying drawings.

SUMMARY OF THE INVENTION

The present invention is directed to a denture bite rim system. One embodiment of the present invention can include a plurality of dental bite rims having a shape and size that is suitable for use in a human mouth. The system can also include a plurality of anatomically correct replica teeth that are constructed from wax. Each of the replica teeth can also include various tooth characteristics such as various shapes, thicknesses, sizes and colors.

In another embodiment, a series of replica teeth are pre-mounted onto one or more of the bite rims in an anatomically correct pattern. In another embodiment, each of the pre-mounted teeth are removably positioned onto the bite rim, and can be removed or adjusted by a dentist.

In yet another embodiment, one or more replica teeth strips can be provided for use with the dental bite rims and/or the replica teeth. Each of the teeth strips can include a front facing surface having the image of one or more teeth imprinted thereon, and a back facing surface that is coated with an adhesive material for mating with one of the dental bite rims.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Figure 1:
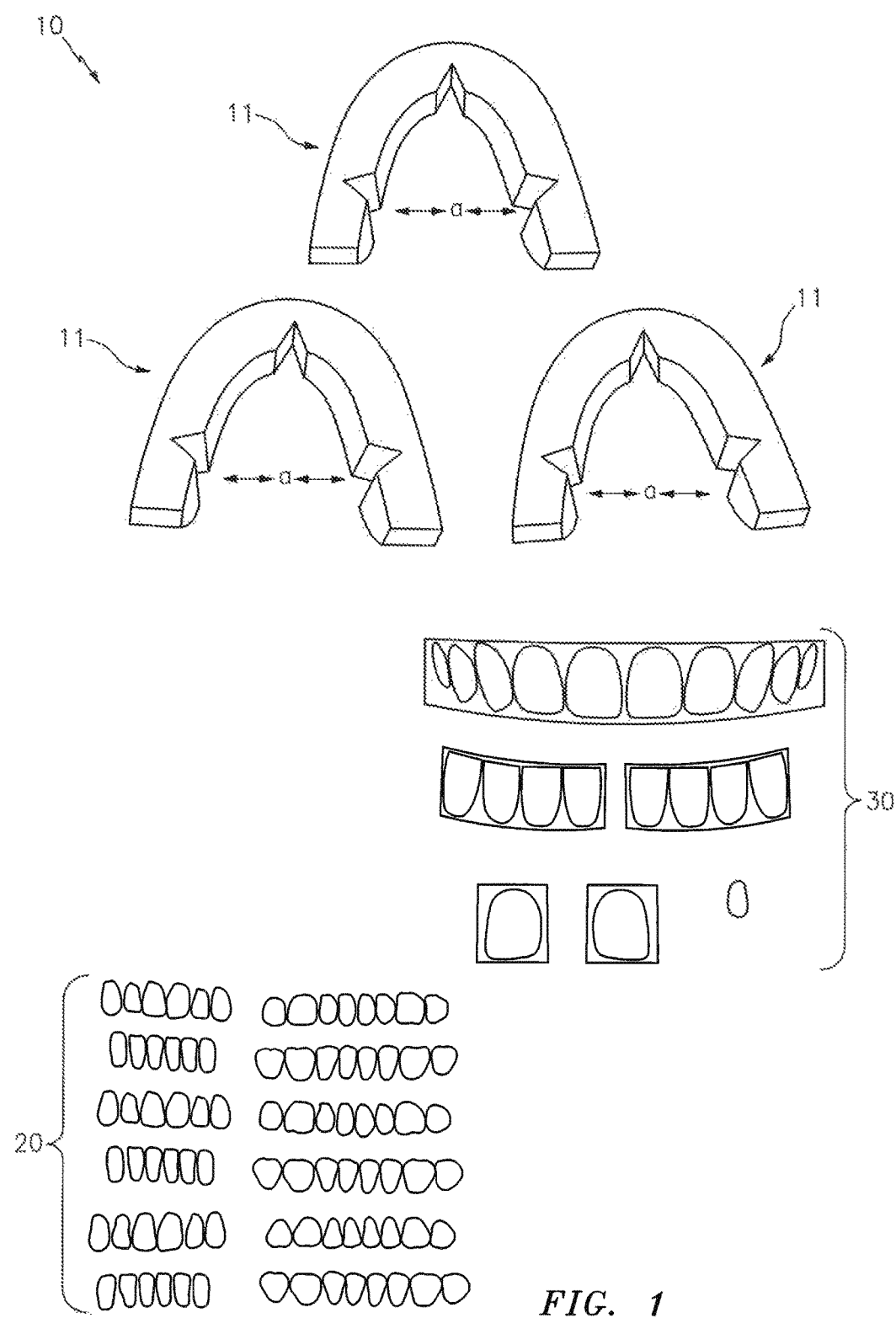
FIG. 1 is an exploded parts view of the denture bite rim system that is useful for understanding the inventive concepts disclosed herein.

Identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

FIGS. 1-3B illustrate one embodiment of a denture bite rim system 10, which is useful for understanding the inventive concepts disclosed herein. As shown, the system 10 can include any number of bite rim bodies 11, a plurality of individual replica teeth 20, and/or a plurality of replica teeth strips 30.

Each bite rim 11 can include a generally U-shaped member having a size that is suitable for use in the upper and/or lower portion of a patient's mouth. The bite rim can be constructed in accordance with known manufacturing techniques and can be made from materials such as bee wax and/or natural paraffin, for example, which are commonly utilized in the construction of dental bite rims.

In one embodiment, one or more of the bite rims can include a plurality of generally triangular shaped notches, each forming a void for allowing the arc of the rim to expand and contract (see arrow a) to conform to the shape of a patients mouth.

The plurality of replica teeth 20 can include any number of individual teeth which can be crafted to represent an anatomically correct whole tooth 21 (e.g., incisor, canines, premolars, molars, etc.). Each tooth can preferably be constructed from colored wax or other similar materials having a low melting point (approximately 125° F.), and can be secured into the bite rim so as to be individually removable in nature. To this end, each tooth 21 can be glued, bonded or pressed into the soft material of the bite rim 11. Of course, other embodiments are contemplated wherein two or more replica teeth are constructed and/or connected together and secured onto the bite rim as described above.

Figure 2A:
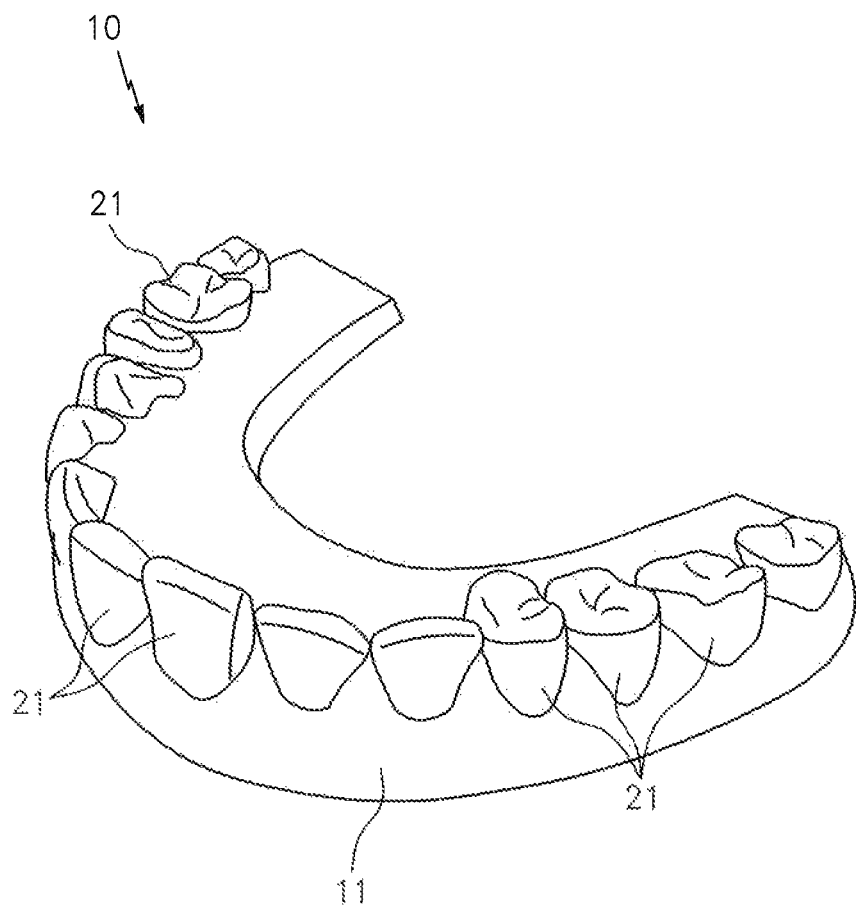
FIG. 2A is a perspective view of one of the bite rims with replica teeth installed thereon, in accordance with one embodiment of the invention.

The system 10 can include any number of individual bite rims 11 which can be provided to a dentist. As shown in FIG. 2A, the bite rims can be provided with a complete or partial set of the replica teeth 21 pre-mounted in the anatomically correct position for use with the upper and/or lower jaw of a patient. Regardless of whether the bite rim is for a lower jaw (FIG. 2A) or an upper jaw (FIG. 2B), each of the replica teeth can be constructed to include characteristics and locations along the bite rim which can be precisely duplicated by the permanent artificial teeth of the final denture.

Such a feature advantageously allows patients to see and choose the particular characteristics of the artificial teeth to be constructed in their final dentures, before the bite rim is sent to the dental laboratory. Such characteristics can include, for example, the shape of each tooth (e.g., oval, square, ovoid or round), the thickness of the tooth (e.g., distance from front to back), and the size of each tooth (e.g., length and width) and/or the color of each tooth.

Figure 2B:
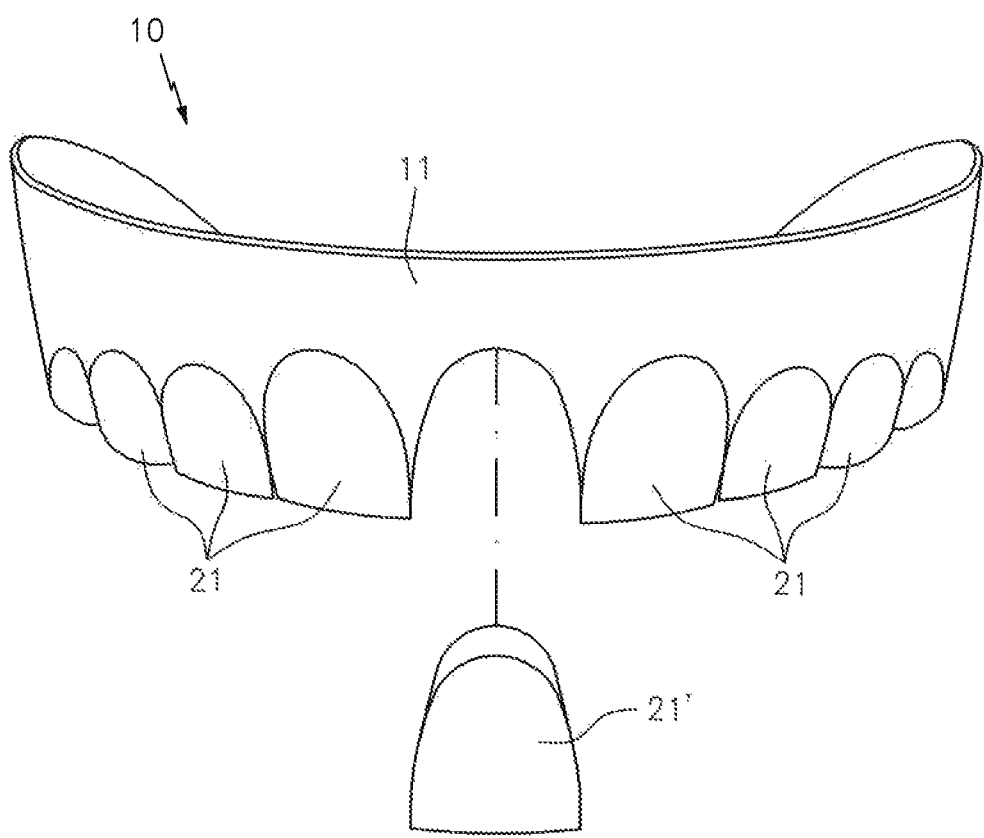
FIG. 2B is another perspective view of one of the bite rims with replica teeth installed thereon, in accordance with one embodiment of the invention.

As shown in FIG. 2B, such a feature also advantageously allows the dentist to shape, and/or adjust each individual replica tooth 21 on a particular bite rim 11, or replace an individual tooth 21 with another such tooth 21' from the provided teeth 20, based on the individual circumstances, needs or desire of the individual patient.

Figure 3A:
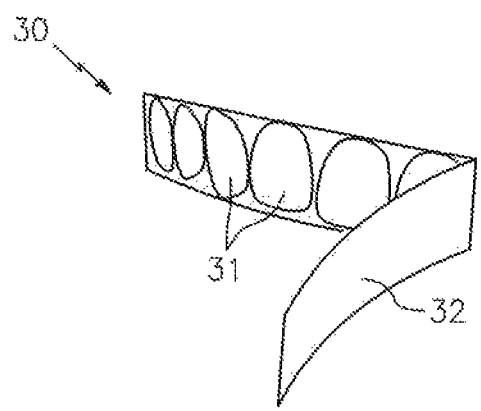
FIG. 3A is a perspective view of one of the replica teeth strips, in accordance with one embodiment of the invention.
Figure 3B:
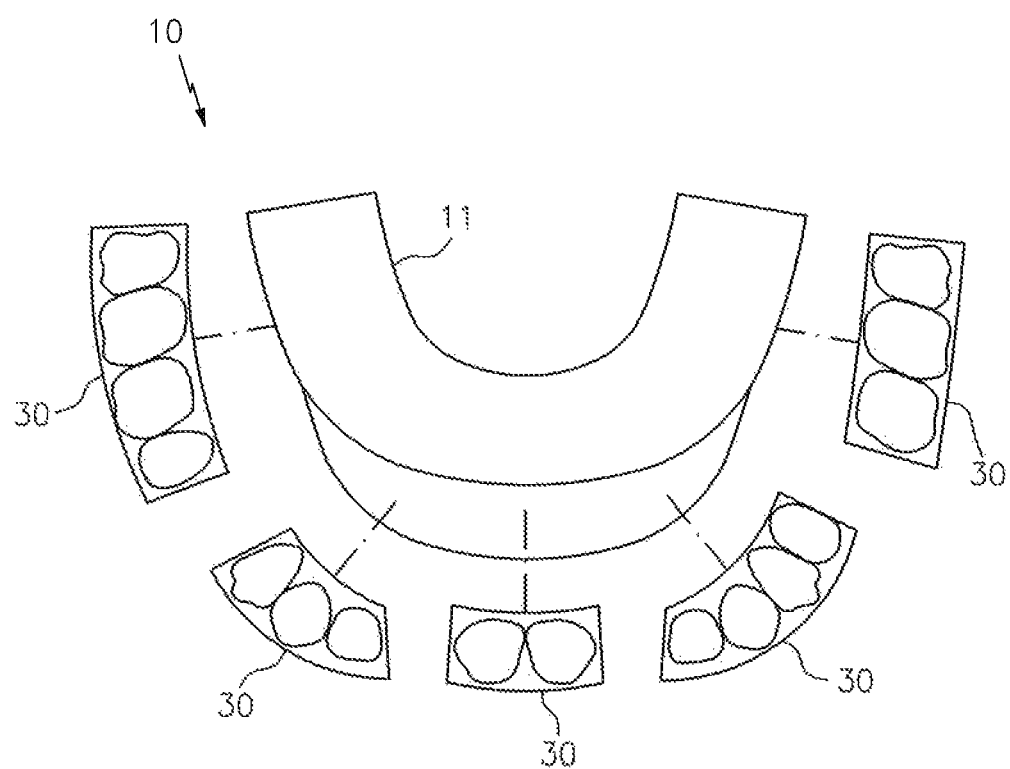
FIG. 3B is a top view of the denture bite rim system in operation, and in accordance with one embodiment of the invention.

Although described above as being constructed from wax, other embodiments are contemplated wherein the replica teeth are constructed from other materials. For example, FIG. 3A illustrates one embodiment of a replica teeth strip 30 which can be constructed from waterproof paper, for example. As shown, the strip can include, or take the form of one or more replica teeth 31 along the front facing side, and can further include an adhesive backing 32. As shown in FIG. 3B, any number of individual teeth strips 30 can be adhered onto a bite rim 11, and can include the same tooth characteristics described above. Such features advantageously allowing dentists to quickly and easily present different tooth characteristics to patients during initial visits. Of course, the strips are not limited to the use of waterproof paper or any particular adhesive materials, as other materials capable of performing the above noted functionality are contemplated.

In either instance, once the bite rim 11 with the replica teeth 21 and/or 31 are acceptable to the patient and dentist, the same can be sent to the dental laboratory wherein each individual replica tooth can be replaced with a permanent denture tooth during the wax try-in stage. In this regard, the dental laboratory can now be provided with a precise guide for crafting the final dentures, and each of the permanent teeth can include the exact type, shape, size and other characteristics that have been pre-selected and approved by the dentist and patient.

Such a feature eliminates the need to make multiple adjustments to the permanent dental teeth, and allows the final set of dentures do be delivered to the patient at the very next appointment.

As described herein, one or more elements of the bite rim system 10 can be secured together utilizing any number of known attachment means. Moreover, although the above embodiments have been described as including separate individual elements, the inventive concepts disclosed herein are not so limiting. To this end, one of skill in the art will recognize that one or more individual elements such as the bite rim, replica teeth 21 and/or teeth strips 30 may be formed together as one continuous element, either through manufacturing processes, such as casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A bite rim system, comprising:
a plurality of flexible and generally U-shaped dental bite rims, each of said rims being constructed solely from wax or paraffin and including a plurality of notches that are disposed along an inside facing surface thereof; and
a plurality of replica teeth, each of said teeth including an anatomically correct whole tooth that is configured to be removably secured onto one of the dental wax bite rims,
wherein each of the plurality of replica teeth are constructed from a wax or paraffin material having a low temperature melting point.

2. The system of claim 1, wherein each of the plurality of replica teeth include tooth characteristics comprising:
a tooth shape, a tooth thickness, a tooth size and a tooth color.

3. The system of claim 2, wherein the plurality of replica teeth include multiple teeth having an identical anatomically correct shape with different tooth characteristics.

4. The system of claim 1, wherein each of the plurality of replica teeth are configured to be pressed into an outside facing surface of one of the plurality of wax bite rims.

5. The system of claim 1, further comprising:
at least one upper jaw wax bite rim having a complete set of replica teeth removably mounted thereon in an anatomically correct position.

6. The system of claim 1, further comprising:
at least one lower jaw wax bite rim having a complete set of replica teeth removably mounted thereon in an anatomically correct position.

7. A bite rim system comprising:
a plurality of flexible and generally U-shaped dental bite rims, each of said rims being constructed solely from wax or paraffin and including a plurality of notches that are disposed along an inside facing surface thereof; and
one or more replica teeth strips, each of said strips including a front surface having one or more individual teeth imprinted thereon; and
an adhesive back surface that is configured to be adhered to an outside facing surface of one of the plurality of dental bite rims,
wherein each of the one or more replica teeth strips are constructed from wax paper having a low temperature melting point.

8. A bite rim system, comprising:
a plurality of flexible and generally U-shaped dental bite rims, each of said rims being constructed solely from wax or paraffin and including a plurality of notches that are disposed along an inside facing surface thereof;
a plurality of replica teeth, each of said teeth including an anatomically correct whole tooth that is configured to be removably secured onto one of the dental wax bite rims;
at least one upper jaw bite rim having a complete set of replica teeth removably mounted thereon in an anatomically correct position; and
at least one lower jaw bite rim having a complete set of replica teeth removably mounted thereon in an anatomically correct position,
wherein said replica teeth are constructed from wax.

* * * * *